United States Patent
Tang (10) Patent No.: US 6,999,550 B2
(45) Date of Patent: Feb. 14, 2006

(54) METHOD AND APPARATUS FOR OBTAINING DATA FOR RECONSTRUCTING IMAGES OF AN OBJECT

(75) Inventor: Xiangyang Tang, Waukesha, WI (US)

(73) Assignee: GE Medical Systems Global Technology, Waukesha, WI (US)

( * ) Notice: Subject to any disclaimer, the term of this patent is extended or adjusted under 35 U.S.C. 154(b) by 109 days.

(21) Appl. No.: 10/774,554

(22) Filed: Feb. 9, 2004

(65) Prior Publication Data

US 2005/0175142 A1 Aug. 11, 2005

(51) Int. Cl.
*A61B 6/03* (2006.01)
(52) U.S. Cl. ......................................... 378/15; 378/901
(58) Field of Classification Search .................. 378/15, 378/901
See application file for complete search history.

(56) References Cited

U.S. PATENT DOCUMENTS

| | | | |
|---|---|---|---|
| 5,216,601 A | 6/1993 | Crawford et al. |
| 5,233,518 A | 8/1993 | King et al. |
| 5,270,923 A | 12/1993 | King et al. |
| 5,280,428 A | 1/1994 | Wu et al. |
| 5,420,788 A | 5/1995 | Vissers |
| 5,461,650 A | 10/1995 | Tam |
| 5,491,735 A | 2/1996 | Hsieh |
| 5,625,190 A | 4/1997 | Crandall |
| 6,009,140 A | 12/1999 | Hsieh |
| 6,101,235 A | 8/2000 | Zavaljevski et al. |
| 6,115,048 A | 9/2000 | Cline et al. |
| 6,137,856 A | 10/2000 | Lin |
| 6,148,056 A | 11/2000 | Lin et al. |
| 6,219,060 B1 | 4/2001 | Ludke et al. |
| 6,256,370 B1 | 7/2001 | Yavuz |
| 6,285,732 B1 | 9/2001 | Hsieh |
| 6,307,908 B1 | 10/2001 | Hu |
| 6,353,653 B1 | 3/2002 | Edic |
| 6,411,670 B1 | 6/2002 | Besson |
| 6,522,712 B1 | 2/2003 | Yavuz et al. |

(Continued)

OTHER PUBLICATIONS

Ge Wang, Tein-Hsiang Lin, Ping-Chin Cheng, and Douglas M. Shinozaki: "A General Cone-Beam Reconstruction Algorithm"; *EEEE Transactions of Medical Imaging*; pp. 486-496; vol. 12: No. 3: Sep. 1993.

(Continued)

*Primary Examiner*—David V Bruce
(74) *Attorney, Agent, or Firm*—Carl B. Horton, Esq.; Armstrong Teasdale LLP (57) ABSTRACT

A method for obtaining data useful for reconstructing an image of an object includes performing a cone beam helical Computed Tomography (CT) scan of an object to obtain projection data from a plurality of detector rows, and interpolating the obtained projection data to generate interpolated data along at least one curve that crosses at least two detector rows.

29 Claims, 7 Drawing Sheets

U.S. PATENT DOCUMENTS

| | | |
|---|---|---|
| 2001/0033682 A1 | 10/2001 | Robar et al. |
| 2001/0048731 A1 | 12/2001 | Nakamura et al. |
| 2002/0118790 A1 | 8/2002 | Pan et al. |
| 2002/0122529 A1 | 9/2002 | Heuscher |
| 2003/0031289 A1 | 2/2003 | Hsieh |
| 2003/0035513 A1 | 2/2003 | Horiuchi |
| 2003/0055328 A1 | 3/2003 | Paladini |
| 2003/0123720 A1 | 7/2003 | Launay et al. |
| 2003/0161434 A1 | 8/2003 | Rand et al. |
| 2003/0185427 A1 | 10/2003 | Hsieh et al. |
| 2003/0194048 A1 | 10/2003 | De Man et al. |
| 2003/0220562 A1 | 11/2003 | Sasaki et al. |
| 2004/0017370 A1 | 1/2004 | Miyamoto et al. |
| 2004/0042588 A1 | 3/2004 | Janes |

OTHER PUBLICATIONS

Carl R. Crawford and Kevin F. King; "Computed Tomography Scanning with Simultaneous Patent Translation": *Med. Phys.*; pp. 967-982; vol. 17; No. 6: Nov./Dec. 1990.

L.A. Feldkamp, L.C. Davis and J.W. Kress; "Practical Cone-Beam Algorithm": *Journal of Optical Seociety, AM. A*; pp. 612-619; vol. 1; No. 6; Jun. 1984.

METHOD AND APPARATUS FOR OBTAINING DATA FOR RECONSTRUCTING IMAGES OF AN OBJECT

BACKGROUND OF THE INVENTION

This invention relates generally to computerized imaging systems and more particularly to methods and apparatus for processing data obtained from such imaging systems.

Two-dimensional (2D) filtered back-projection (FBP) reconstruction algorithms are efficient computationally and provide robust imaging performance. Thus, these algorithms are commonly used in CT imaging apparatus, even though CT has progressed from conventional fan beam (FB) scanners to state-of-the-art multi-detector-row scanner. Volumetric CT (VCT) scanners are among the most recent developments in CT imaging apparatus. In VCT scanners, three-dimensional (3D) or cone beam (CB) FBP reconstruction algorithms are used. One practical CB FBP reconstruction algorithm (FDK) has been described by Feldkamp et al. in "Practical cone-beam algorithm," J. Opt. Soc. A., Vol. 1, pp. 612–619, 1984. The original FDK has been heuristically extended from its 2D FB counterpart to the CB case based upon a circular source trajectory, in which a one-dimensional (1D) row-wise ramp filtering and 3D back-projector are used. Subsequently, the FDK algorithm has been extended to handle the helical CB data acquisition geometry (namely helical FDK), in which a row-wise 1D ramp filtering is still used, as described by Wang et al. in "A general cone-beam reconstruction algorithm," IEEE Trans. Med. Imag., vol. 12, pp. 486–496, 1993. In principal, the helical FDK algorithm is an approximate CB reconstruction algorithm, even though a helical source trajectory satisfies the so-called data sufficiency condition. The helical FDK can satisfactorily eliminate artifacts caused by cone beam angle due to the utilization of 3D back-projection under small to medium cone angle. However, the suppression of helical artifacts, such as streak, shading/glaring and geometric distortion caused by data inconsistencies in helical data acquisition, is not as satisfactory. To suppress helical artifacts, adequate helical view weighting strategies before filtering have to be exercised, as described by Crawford et al., "Computed tomography scanning with simultaneous patient translation," Med. Phys. 17(6), pp. 967–982, 1990.

Exact helical CB reconstruction algorithms offer theoretically accurate CB reconstruction capability. However, exact helical CB reconstruction algorithms have various disadvantages that may include non-FBP computational structure; poor spatial resolution; poor noise characteristics; or poor computational efficiency.

BRIEF DESCRIPTION OF THE INVENTION

Some configurations of the present invention therefore provide a method for obtaining data useful for reconstructing an image of an object. The method includes performing a cone beam helical Computed Tomography (CT) scan of an object to obtain projection data from a plurality of detector rows, and interpolating the obtained projection data to generate interpolated data along at least one curve that crosses at least two detector rows.

In other aspects, the present invention provides a computed tomographic (CT) imaging apparatus having a multi-row detector. The imaging apparatus is configured to perform a cone beam helical scan of an object to obtain projection data from a plurality of detector rows, and interpolate the obtained projection data to generate interpolated data along at least one curve that crosses at least two detector rows.

In yet another aspect, the present invention provides a computer-usable medium having a computer-readable program embodied thereon. The program is configured to instruct a computer to interpolate projection data of a scan of an object obtained from a plurality of rows of a detector array of a cone beam helical Computed Tomography (CT) apparatus. The interpolation is configured to generate interpolated data along at least one curve that crosses at least two rows of the detector array.

As described herein, various configurations of the present invention outperform other configurations using helical FDK algorithms by significantly suppressing shading and glaring artifacts caused by inconsistencies in helical CB data acquisition in volumetric CT scanners. Also, various configurations of the present invention outperform configurations using the FDK algorithm by significantly suppressing geometric distortion caused by inconsistencies in helical CB data acquisition in volumetric CT scanners.

Some configurations of the present invention also outperform other configurations using an approximate CB reconstruction algorithm, such as the PI-method and related methods, in that better noise characteristics and dose efficiencies are achieved. Also, some configurations of the present invention also outperform other configurations using exact CB reconstruction algorithms in which the Tam-window is used, such as Katsevich's algorithms, from the perspective of noise characteristics and x-ray dose efficiency. Various configurations of the present invention also advantageously provide in-plane spatial resolution matching that of conventional FB reconstruction algorithms and helical FDK algorithm.

BRIEF DESCRIPTION OF THE DRAWINGS

FIG. 8 is an axial view of the same HBP phantom reconstructed using a configuration of a CB RS-FBP reconstruction algorithm of the present invention using rotated-and-shifted 1D ramp filtering. (In FIGS. 7 and 8, W/L=100/0; Phantom: HBP; detector: 64×0.625 mm; radius of detector: 541.0 mm; pitch: 88/64.)

FIG. 10 is an axial view of the same Defrise phantom of FIG. 9 reconstructed using a configuration of a CB RS-FBP reconstruction algorithm of the present invention using rotated 1D ramp filtering. (In FIGS. 9 and 10, W/L=200/0; Phantom: Defrise; detector: 64×0.625 mm; radius of detector: 541.0 mm; pitch: 88/64.)

FIG. 12 is a coronal reformatted view of the same Defrise phantom of FIG. 11 reconstructed using a configuration of a CB RS-FBP reconstruction algorithm of the present invention using rotated 1D ramp filtering. (In FIGS. 11 and 12, W/L=300/0; Phantom: Defrise; detector: 64×0.625 mm; radius of detector: 541.0 mm; pitch: 88/64.)

FIG. 14 is a sagittal reformatted view of the same Defrise phantom of FIG. 13 reconstructed using a configuration of a CB RS-FBP reconstruction algorithm of the present invention using rotated 1D ramp filtering. (In FIGS. 13 and 14, W/L=300/0; Phantom: Defrise; detector: 64×0.625 mm; radius of detector: 541.0 mm; pitch: 88/64.)

DETAILED DESCRIPTION OF THE INVENTION

Example embodiments of systems and methods that facilitate obtaining data useful for reconstructing images of an object are described below in detail. Technical effects of the systems and methods described herein include at least one of rearranging or processing data into forms that are useful for image reconstruction such as by Cone Beam Rotated and Shifted Filtered Back-Projection (CB RS-FBP) image reconstruction, or of reconstructing actual images of an object.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered backprojection algorithm.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 1:
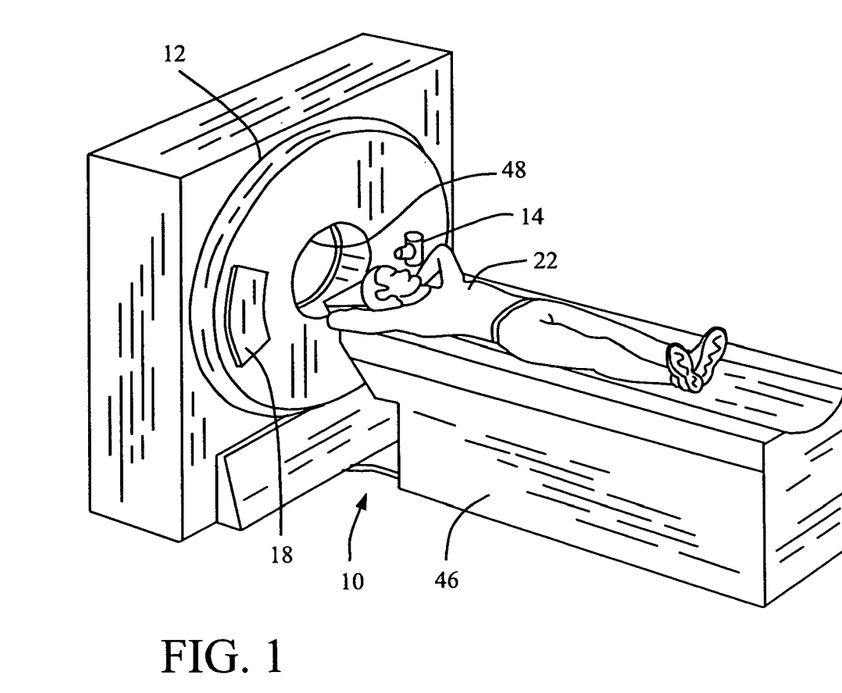
FIG. 1 is a pictorial view representative of configurations of a CT imaging apparatus of the present invention.
Figure 2:
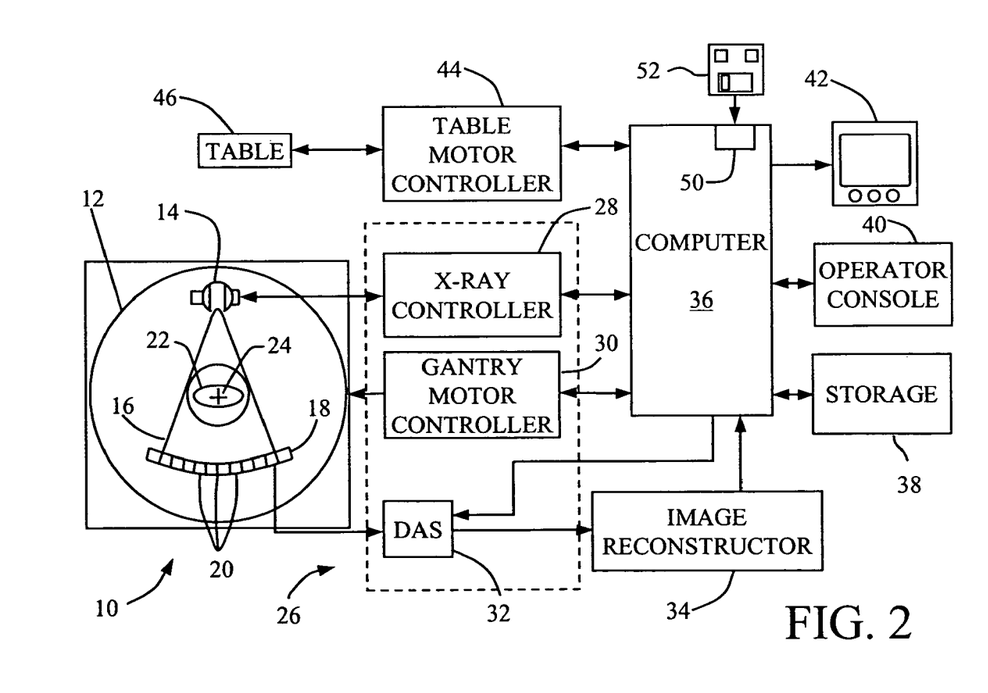
FIG. 2 is a block schematic diagram of the apparatus illustrated in FIG. 1.

Referring to FIGS. 1 and 2, a multi-slice scanning imaging system, for example, a Computed Tomography (CT) imaging system 10, is shown as including a gantry 12 representative of a "third generation" CT imaging system. Gantry 12 has an x-ray tube 14 (also called x-ray source 14 herein) that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22 between array 18 and source 14. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated cathode ray tube display 42 (or any other suitable display device) allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes an instruction-obtaining device 50, for example, a floppy disk drive, CD-ROM drive, DVD drive, magnetic optical disk (MOD) device, or any other digital device including a network connecting device such as an Ethernet device. Instruction-obtaining device 50 is provided to read instructions and/or data from a computer-usable medium 52, such as a floppy disk, a CD-ROM, or a DVD having a computer readable program embodied thereon. The program, in some configurations is configured to instruct a computer, e.g., computer 36, to perform functions described herein and/or send signals to other devices to perform some or all of the functions. In some configurations, instruction-obtaining device 50 obtains program instructions from another digital source such as a network or the Internet, or yet to be developed digital means. In another embodiment, computer 36 executes instructions stored in firmware (not shown). Computer 36 is programmed to perform functions described herein and/or send signals to other devices to perform some or all of the functions. As used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Although the specific embodiment mentioned above refers to a third generation CT system, the methods described herein equally apply to fourth generation CT systems (stationary detector—rotating x-ray source) and fifth generation CT systems (stationary detector and x-ray source). Additionally, it is contemplated that the benefits of the invention accrue to imaging modalities other than CT. Additionally, although the herein described methods and apparatus are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center.

Figure 3:
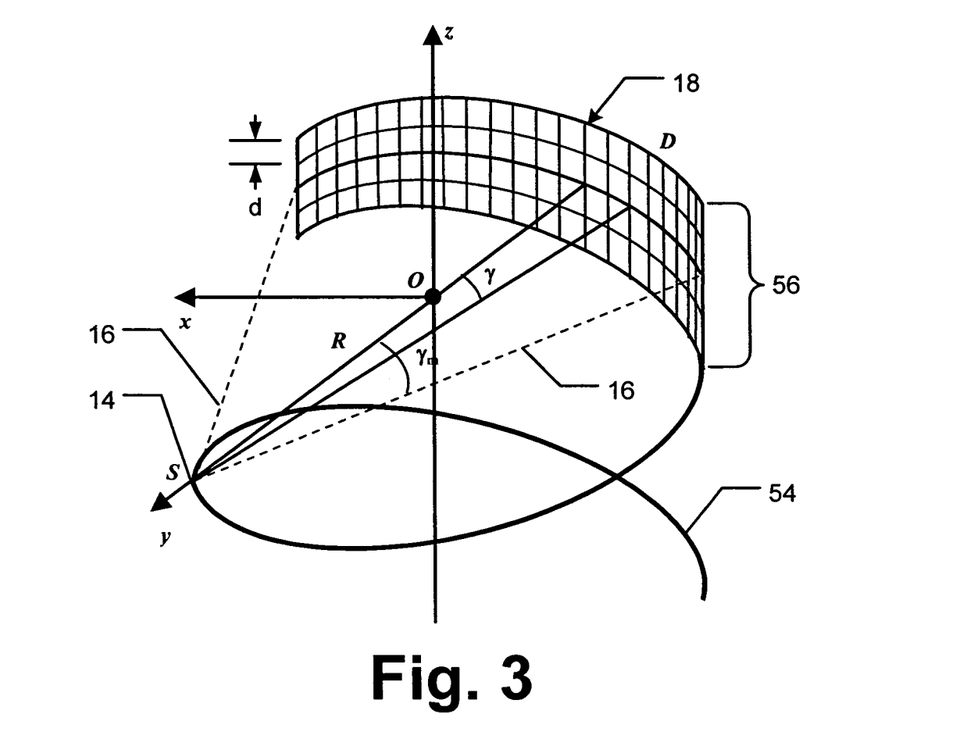
FIG. 3 is a diagram showing geometry of helical cone beam projection data acquisition and backprojection, wherein $\gamma_m$ is a horizontal maximum half cone angle.
Figure 4:
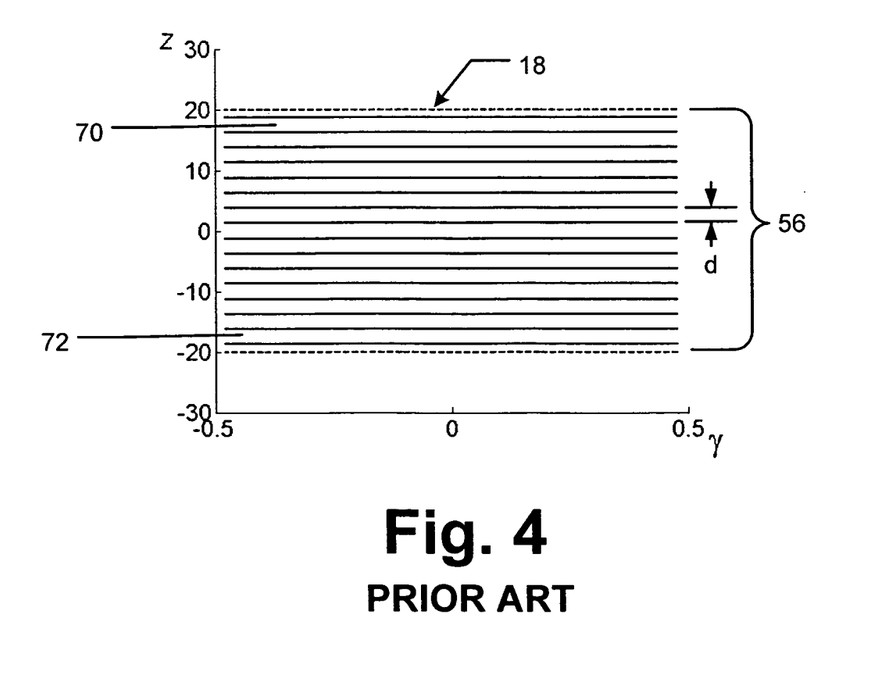
FIG. 4 is a diagram showing detector rows of a typical prior art cylindrical detector (16×2.5 mm) in a volumetric CT.

When apparatus 10 is used as a volumetric CT scanner, the perspective geometry of the helical source trajectory and projection data acquisition in a volumetric CT scanner is shown in FIG. 3, where (x, y, z) represents the local coordinate system, S is source 14 focal spot, D is a cylindrical multi-row CT detector array 18, R is the radius of cylindrical detector array 18 and y is the fan angle of an x-ray beam 16. A prior art cylindrical multi-row CT detector array 18 is represented in FIG. 4 as a plurality of rows 56. (Individual detector elements 20 are not shown in FIG. 4.) Detector rows 56 in the prior art detector array 18 represented in FIG. 4 correspond to intersections between cylindrical detector array 18 and a family of planes not shown in FIG. 4 but written as:

$$z_i = b_i, i=0, 1, \ldots N-2, N-1, \qquad (1)$$

where $$b_i = (i-N/2+0.5)d, =0, 1, \ldots N-2, N-1, \qquad (2)$$

d is the height of a detector row 56, and

N (usually an even number) is the total number of detector rows 56.

In prior art helical FDK reconstructions, 1D ramp filtering is implemented along horizontal detector rows 56.

Source 14 displacement per rotation in helical CB data acquisition is written as:

$$H = hNd, \qquad (3)$$

where h is the helical pitch. Subsequently, the tangential of the helical source 14 trajectory is written:

$$\tan \eta_0 = \frac{H}{2\pi R} = \frac{hNd}{2\pi R}. \qquad (4)$$

Figure 5:
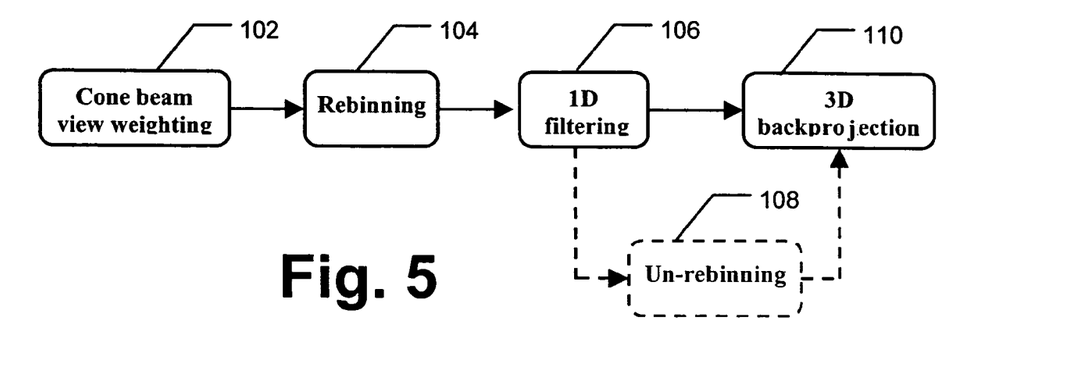
FIG. 5 is a flow-chart representative of various configurations of a cone beam rotated and shifted filtered back-projection (CB RS-FBP) reconstruction algorithm using rotated-and-shifted 1D ramp filtering across detector rows.
Figure 6:
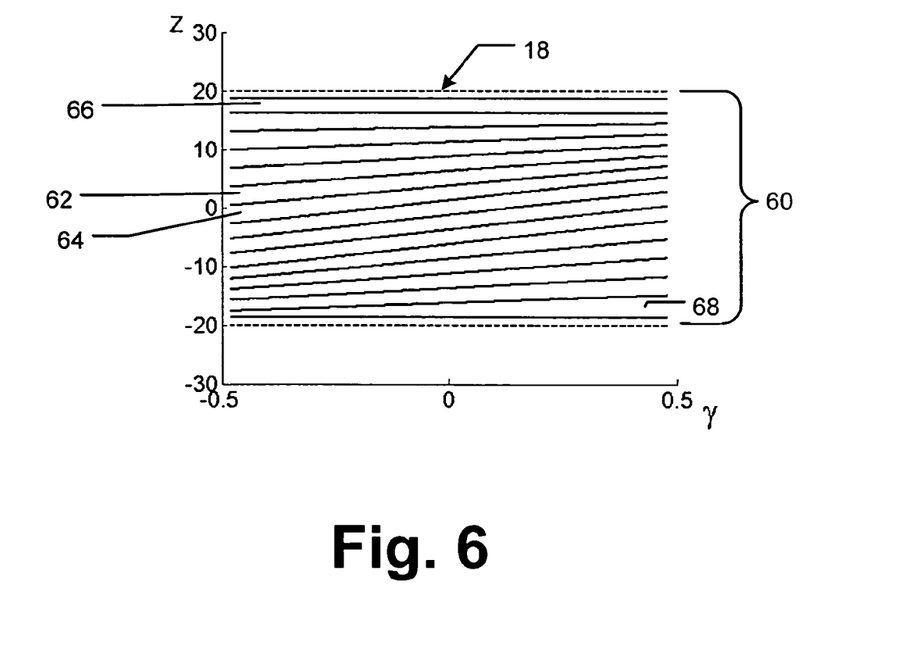
FIG. 6 is a schematic showing a family of curves across detector rows in a cylindrical detector (16×2.5 mm), along which the 1D ramp filtering of the CB RS-FBP reconstruction algorithm of FIG. 5 is applied before 3D backprojection.

In some configurations of the present invention, a cone beam helical scan is performed using CT imaging apparatus 10 to scan object 22 to obtain projection data from a plurality of rows 56 of detector array 18. Next, a procedure is initiated, for example, by a user operating apparatus 10 so that computer 36 further processes the data to achieve one or more technical effects, including the obtaining of data useful for reconstructing an image of object 22. An example of one such procedure configuration is represented by flow chart 100 of FIG. 5, wherein cone beam view weighting of the projection data to handle data redundancy is first performed at 102. Cone beam weighting 102, for example, may be performed in a manner described by the Crawford et al. publication referred to above. Rotated-and-shifted ramp filtering is then performed using a cascade of rebinning 104 and ramp filtering 106. Rebinning 104 is used to interpolate the obtained, weighted projection data to generate interpolated data along at least one curve crossing at least two detector rows. Referring to FIGS. 4 and 6, projection data acquired by cylindrical detector 18 are interpolated by rebinning 104 into a 2D data array along a family of curves 60 across detector rows 56. To maintain in-plane spatial resolution, only 1D interpolation along the z-axis is used. Curves in curve family 60 are the intersections between cylindrical detector 18 and a plane family not shown in the Figures but written as:

$$z_i = k_i x + b_i, i=0, 1, \ldots N-2, N-1, \qquad (5)$$

where $$k_0 = k_N = 0, \qquad (6)$$

$$k_{N/2-1} = k_{N/2} = \tan \eta_0, \qquad (7)$$

$$k_i = \frac{\frac{N}{2} - 2 - \left|i - \frac{N}{2} + 2\right|}{\frac{N}{2} - 2} \tan \eta_0, \quad (8)$$

$$i = 1, 2, \cdots \frac{N}{2} - 3, \frac{N}{2} - 2,$$

$$k_i = \frac{\frac{N}{2} - 2 - \left|i - \frac{N}{2} - 1\right|}{\frac{N}{2} - 2} \tan \eta_0, \quad (9)$$

$$i = \frac{N}{2} + 1, \frac{N}{2} + 2, \cdots N - 3, N - 2.$$

Only the central two planes corresponding to central curve 62 and central curve 64 are parallel to the tangential direction of the helical source trajectory. Uppermost plane corresponding to uppermost curve 66 and lowermost plane corresponding to lowermost curve 68 coincide with uppermost detector row 70 and lowermost detector row 72 of FIG. 4, respectively. The slopes of all other planes in the plane family are between the tangential of the helical source trajectory and zero by a gradual rotation. Consequently, in some configurations, rebinning results in interpolation of obtained projection data to generate interpolated data along a plurality of curves that cross at least two detector rows, such that at least two of the curves are non-parallel. In some configurations, the plurality of curves include two central curves (e.g., curve 62 and curve 64), two exterior curves (e.g., curve 66 and curve 68), and a plurality of intermediate curves 76 that cross at least two detector 18 rows (e.g., rows 56 other than rows 70 and 72), such that at least two central curves are parallel to each other and all intermediate curves are nonparallel to each other, the two central curves, and the two exterior curves. Curves across detector rows 56 upon which the obtained projection is interpolated to generate at least one curve that crosses two detector rows are generated in some configurations of the present invention in accordance with an expression written as:

$$z_i = k_i R \sin(\gamma) + b_i, i = 0, 1, \ldots N-2, N-1, \quad (10)$$

where $z_i$ represents a plane intersecting cylindrical detector 18.

To maintain spatial resolution along the z-axis, an up-sampling of factor 2 or higher is used in some configurations in rebinning at 104. For instance, if the up-sampling factor is 2, there are 128 rotated-and shifted curves in the rebinned data array, while there are only 64 rows in detector array 18 (not all of which are shown in the Figures herein).

After the CB projection data is rebinned at 104, a one-dimensional (1D) ramp filtering is applied at 106 one-by-one along each curve. The subsequent inverse rebinning (or "un-rebinning") sub-process 108 is an inversion of rebinning sub-process 104 prior to filtering 106, which maps the filtered data on the rebinned array corresponding to curves 60 of FIG. 6 back to an original array corresponding to detector rows 56 of FIG. 4. Again, only 1D interpolation along the z-axis is needed. In fact, inverse rebinning sub-process 108 is not required in many configurations, because 3D backprojection 110 can be carried out using the filtered CB projection data located on either the original data array or the rebinned data array.

As can be seen in FIG. 6, all the projection data within cylindrical detector array 18 can be used for reconstruction, because all those rotated and/or shifted curves 60 are always within cylindrical detector 18. Therefore, CB RS (Rotated and Shifted)-FBP reconstruction configurations of the present invention provide superior noise characteristics and dose efficiency compared to other configurations using CB reconstruction algorithms in which the Tam-window is used, such as the approximate PI-method and its derivatives, as well as the exact algorithms derived by Katsevich. Because rotated-and-shifted curves 60 always locate within cylindrical detector 18, no projection data truncation occurs. Consequently, extra artifacts associated with data truncation can be avoided.

Figure 7:
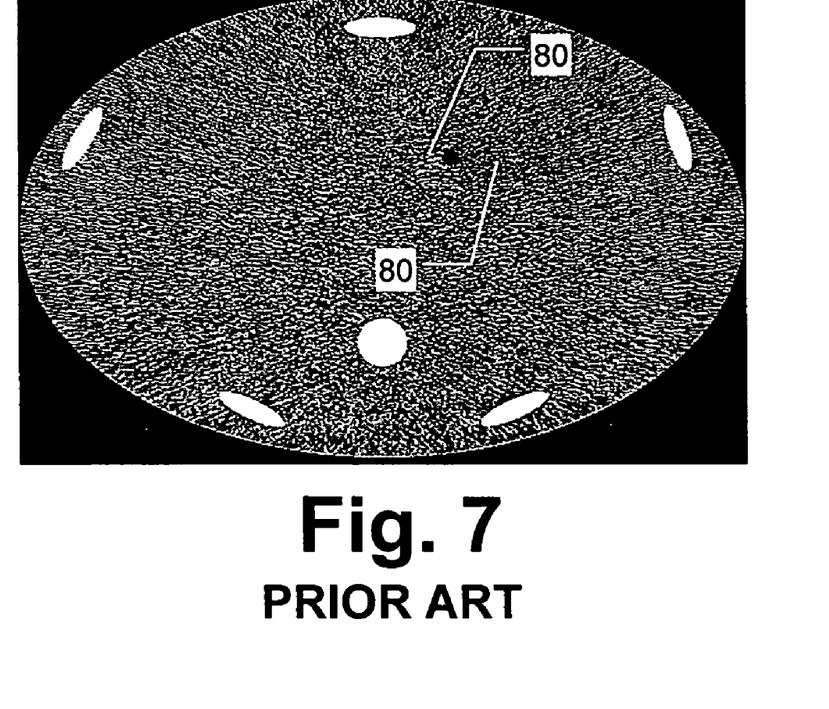
FIG. 7 is an axial view of a HBP phantom reconstructed using a prior art helical FDK algorithm.
Figure 8:
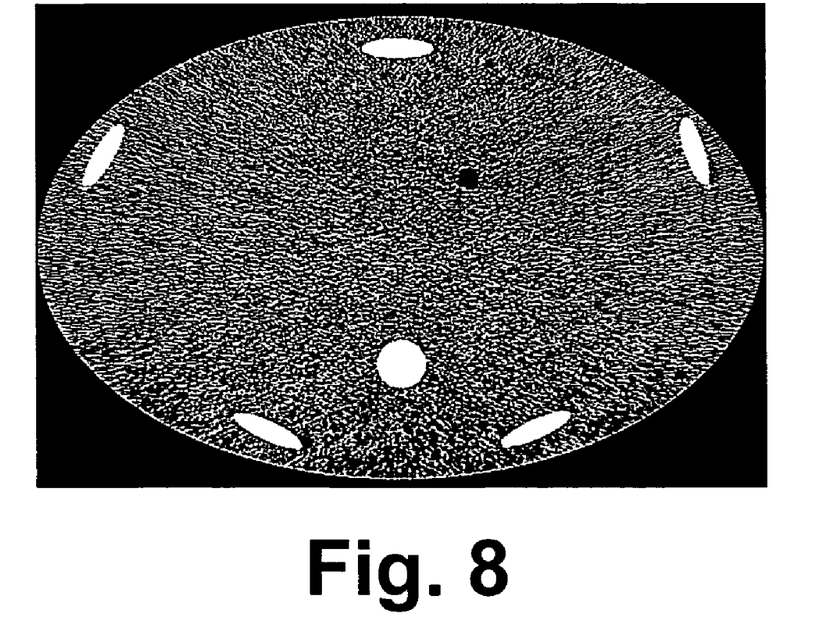

Three examples are provided herein that show improvement in reconstruction accuracy offered by configurations of the present invention over imaging performance using the helical FDK algorithm. In FIG. 7 and FIG. 8, a helical body phantom was imaged. A shading/glaring artifact 80 existing in the axial image of the HBP phantom reconstructed by the helical FDK algorithm in FIG. 7 is almost eliminated in an image reconstructed using a configuration of the present invention shown in FIG. 8. FIG. 8 utilizes a configuration of CB RS-FBP reconstruction algorithm described herein using rotated-and-shifted 1D ramp filtering (W/L=100/0; Phantom: HBP; detector: 64×0.625 mm; radius of detector: 541.0 mm; pitch: 88/64).

Figure 9:
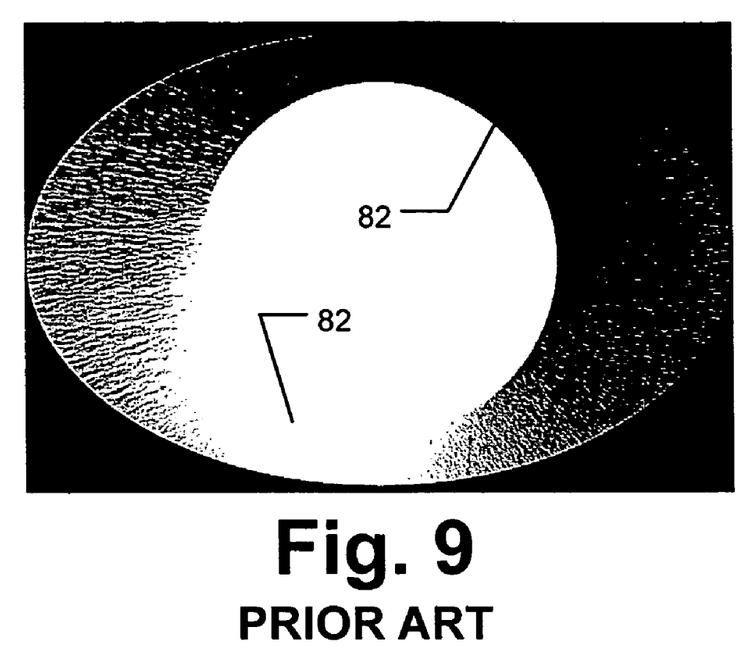
FIG. 9 is an axial view of a Defrise phantom reconstructed using a prior art helical FDK algorithm.
Figure 10:
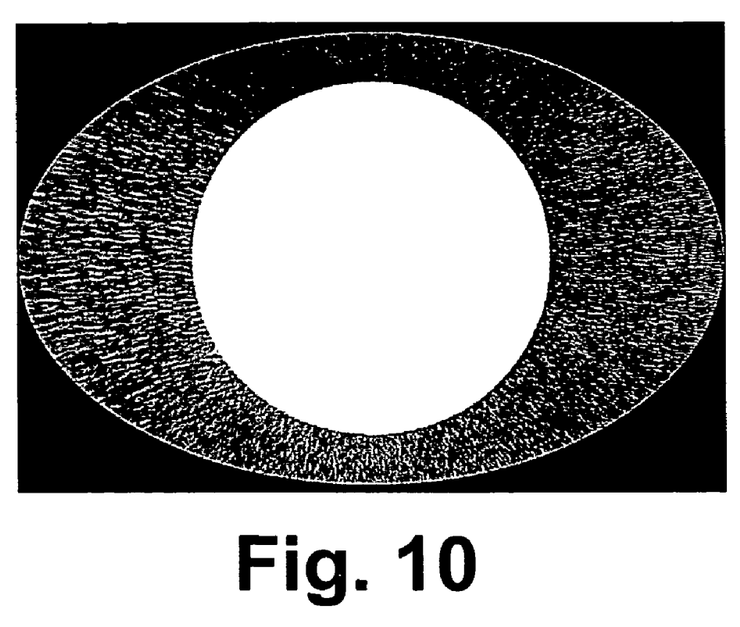

In FIGS. 9 and 10 (and all subsequent Figures) a Defrise phantom is used. FIG. 9 illustrates very severe shading/glaring artifacts 82 existing in the axial view of the Defrise phantom reconstructed by the helical FDK algorithm. These artifacts are significantly reduced or eliminated utilizing a CB RS-FBP reconstruction algorithm using rotated 1D ramp filtering configuration of the present invention (W/L=200/0; Phantom: Defrise; detector: 64×0.625 mm; radius of detector: 541.0 mm; pitch: 88/64) as illustrated by FIG. 10.

Figure 11:
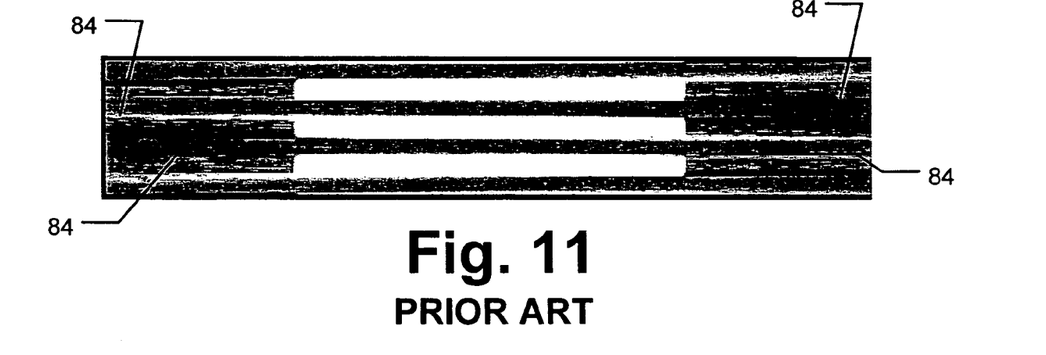
FIG. 11 is a coronal reformatted view of a Defrise phantom reconstructed using a prior art helical FDK algorithm.
Figure 12:
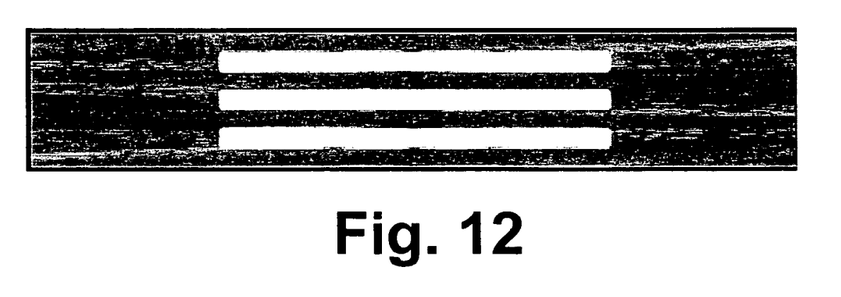

FIGS. 11 and 12 show a comparison of shading/glaring artifacts and geometric distortion in coronal reformatted views. FIG. 11 was reconstructed by a helical FDK algorithm. Substantial artifacts 84 are shown, some of which are indicated in the Figure. FIG. 12 was reconstructed using a configuration of the CB RS-FBP reconstruction algorithm disclosed herein using rotated 1D ramp filtering (W/L=300/0; Phantom: Defrise; detector: 64×0.625 mm; radius of detector: 541.0 mm; pitch: 88/64).

Figure 13:
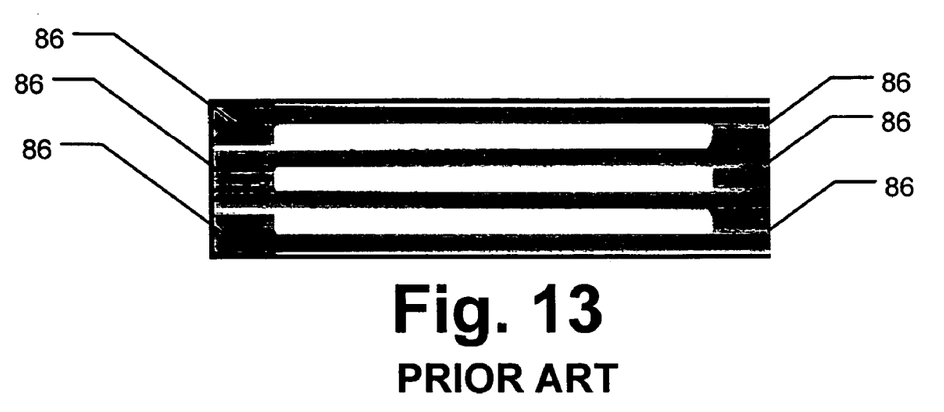
FIG. 13 is a sagittal reformatted view of a Defrise phantom reconstructed using a prior art FDK algorithm.
Figure 14:
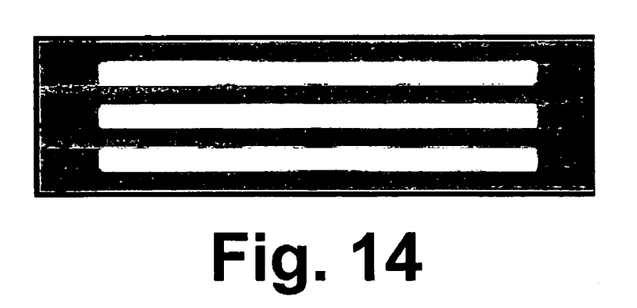

FIGS. 13 and 14 show a comparison of the capability of suppressing shading/glaring artifacts and geometric distortion in the sagittal reformatted views. FIG. 13 was reconstructed by a helical FDK algorithm.and shows substantial artifacts 86. FIG. 13 was reconstructed using a configuration of CB RS-FBP reconstruction algorithm disclosed herein using rotated 1D ramp filtering. (W/L=300/0; Phantom: Defrise; detector: 64×0.625 mm; radius of detector: 541.0 mm; pitch: 88/64).

Configurations of the present invention outperform other configurations using helical FDK algorithms by significantly suppressing shading and glaring artifacts caused by inconsistencies in helical CB data acquisition in volumetric CT scanners. Also, configurations of the present invention outperform configurations using the FDK algorithm by significantly suppressing geometric distortion caused by inconsistencies in helical CB data acquisition in volumetric CT scanners.

Configurations of the present invention also outperform other configurations using an approximate CB reconstruction algorithm, such as the PI-method and related methods, in that better noise characteristics and dose efficiencies are achieved. Configurations of the present invention also outperform other configurations using exact CB reconstruction algorithms in which the Tam-window is used, such as Katsevich's algorithms, from the perspective of noise characteristics and x-ray dose efficiency. Configurations of the present invention also provide in-plane spatial resolution matching that of conventional FB reconstruction algorithms and helical FDK algorithm.

It will be appreciated that configurations of the present invention are not limited to cylindrical detector geometries, and that other detector geometries can be used in other configurations of the present invention. Helical reconstruction algorithms disclosed herein using rotational filtering can be used with any detector geometry. For example, in some configurations, a multirow flat panel detector array is used, such as is used extensively in volumetric CT imaging technology.

While the invention has been described in terms of various specific embodiments, those skilled in the art will recognize that the invention can be practiced with modification within the spirit and scope of the claims.

What is claimed is:

1. A method for obtaining data useful for reconstructing an image of an object, said method comprising:
performing a cone beam helical Computed Tomography (CT) scan of an object to obtain projection data from a plurality of detector rows; and
interpolating the obtained projection data to generate interpolated data along at least one curve that crosses at least two detector rows.

2. A method in accordance with claim 1 further comprising performing a one dimensional filtering of said interpolated data along each said curve.

3. A method in accordance with claim 1, wherein said interpolating the obtained data to generate interpolated data along at least one curve includes rebinning the obtained projection data, and further comprising ramp filtering of said interpolated data along each said curve.

4. A method in accordance with claim 3 further comprising performing a three dimensional backprojection on the rebinned projection data to generate an image.

5. A method in accordance with claim 3 further comprising:
un-rebinning the filtered data along each said curve to generate an un-rebinned dataset; and
performing a three dimensional backprojection on the un-rebinned dataset to generate an image.

6. A method in accordance with claim 1, wherein said interpolating the obtained projection data comprises interpolating the obtained projection data to generate interpolated data along a plurality of curves that cross at least two detector rows such that at least two curves are nonparallel.

7. A method in accordance with claim 1, wherein said interpolating the obtained projection data comprises interpolating the obtained projection data to generate a plurality of curves including two central curves, two exterior curves, and a plurality of intermediate curves between each central curve and a corresponding exterior curve, wherein the central curves and the intermediate curves cross at least two detector rows and the two exterior curves do not cross at least two detector rows, such that at least two central curves are parallel to each other and all the intermediate curves are non parallel each other, the two central curves, and the two exterior curves.

8. A method in accordance with claim 7 wherein said interpolating the obtained projection data to generate at least one curve that crosses at least two detector rows comprises generating a plurality of curves in accordance with:

$z_i = k_i R \sin(\gamma) + b_i, i = 0, 1, \ldots N-2, N-1,$ where z represents a plane intersecting the detector, said detector being a cylindrical detector, $k_0 = k_N = 0,$ $k_{N/2}^{-1} = k_{N/2} = \tan \eta_0,$ $$k_i = \frac{\frac{N}{2} - 2 - \left|i - \frac{N}{2} + 2\right|}{\frac{N}{2} - 2} \tan \eta_0 \quad i = 1, 2, \cdots \frac{N}{2} - 3, \frac{N}{2} - 2,$$

and $$k_i = \frac{\frac{N}{2} - 2 - \left|i - \frac{N}{2} - 1\right|}{\frac{N}{2} - 2} \tan \eta_0 \quad i = \frac{N}{2} + 1, \frac{N}{2} + 2, \cdots N - 3, N - 2,$$

wherein N is the number of detector rows of the cylindrical detector, and $\tan \eta_0 = (hNd)/(2\pi R)$ where h is a helical pitch, d is a detector row height, and R is a radius of the detector.

9. A method in accordance with claim 7 wherein said interpolating the obtained projection data comprises rebinning data using an up-sampling factor of at least 2.

10. A method in accordance with claim 1 wherein said detector is a flat panel detector.

11. A computed tomographic (CT) imaging apparatus having a multirow detector, said imaging system configured to:
perform a cone beam helical scan of an object to obtain projection data from a plurality of detector rows; and
interpolate the obtained projection data to generate interpolated data along at least one curve that crosses at least two detector rows.

12. An apparatus in accordance with claim 11 further configured to perform a one dimensional filtering of said interpolated data along each said curve.

13. An apparatus in accordance with claim 11, wherein to interpolate the obtained data to generate interpolated data along at least one curve, said apparatus is configured to rebin the obtained projection data, and said apparatus is configured to ramp filter said interpolated data along each said curve.

14. An apparatus in accordance with claim 13 further configured to perform a three dimensional backprojection on the rebinned projection data to generate an image.

15. An apparatus in accordance with claim 13 further configured to:
un-rebin the filtered data along each said curve to generate an un-rebinned dataset; and
perform a three dimensional backprojection on the un-rebinned dataset to generate an image.

16. An apparatus in accordance with claim 11, wherein to interpolate the obtained projection data, said apparatus is configured to interpolate the obtained projection data to generate interpolated data along a plurality of curves that cross at least two detector rows such that at least two curves are nonparallel.

17. An apparatus in accordance with claim 11, wherein to interpolate the obtained projection data, said apparatus is configured to interpolate the obtained projection data to generate a plurality of curves including two central curves, two exterior curves, and a plurality of intermediate curves between each central curve and a corresponding exterior curve, wherein the central curves and the intermediate curves cross at least two detector rows and the two exterior curves do not cross at least two detector rows, such that at least two central curves are parallel to each other and all the intermediate curves are non parallel each other, the two central curves, and the two exterior curves.

18. An apparatus in accordance with claim 17 wherein to interpolate the obtained projection data to generate at least one curve that crosses at least two detector rows, said apparatus is configured to generate a plurality of curves in accordance with:

$$z_i = k_i R \sin(\gamma) + b_i, i=0, 1, \ldots N-2, N-1,$$

where z represents a plane intersecting said detector, which is a cylindrical detector, $$k_0 = k_N = 0,$$

$$k_{N/2-1} = k_{N/2} = \tan \eta_0,$$

$$k_i = \frac{\frac{N}{2} - 2 - \left|i - \frac{N}{2} + 2\right|}{\frac{N}{2} - 2} \tan \eta_0 \quad i = 1, 2, \cdots \frac{N}{2} - 3, \frac{N}{2} - 2,$$

and $$k_i = \frac{\frac{N}{2} - 2 - \left|i - \frac{N}{2} - 1\right|}{\frac{N}{2} - 2} \tan \eta_0 \quad i = \frac{N}{2} + 1, \frac{N}{2} + 2, \cdots N-3, N-2,$$

wherein N is the number of detector rows of the cylindrical detector, and $\tan \eta_0 = (hNd)/(2\pi R)$ where h is a helical pitch, d is a detector row height, and R is a radius of the detector.

19. An apparatus in accordance with claim 17 wherein to interpolate the obtained projection data, said apparatus is configured to rebin data using an up-sampling factor of at least 2.

20. An apparatus in accordance with claim 11 wherein said detector is a flat panel detector.

21. A computer-usable medium having a computer-readable program embodied thereon, said program configured to instruct a computer to interpolate projection data of a scan of an object obtained from a plurality of rows of a detector array of a cone beam helical Computed Tomography (CT) apparatus, said interpolation configured to generate interpolated data along at least one curve that crosses at least two rows of said detector array.

22. A medium in accordance with claim 21 wherein said program is further configured to instruct the computer to perform a one dimensional filtering of said interpolated data along each said curve.

23. A medium in accordance with claim 21, wherein to interpolate the obtained data to generate interpolated data along at least one curve, said program is configured to instruct the computer to rebin the obtained projection data, and to perform said one dimensional filtering, said program is configured to instruct the computer to ramp filter said interpolated data along each said curve.

24. A medium in accordance with claim 23 wherein said program is further configured to instruct the computer to perform a three dimensional backprojection on the rebinned projection data to generate an image.

25. A medium in accordance with claim 23 wherein said program is further configured to instruct the computer to:
   un-rebin the filtered data along each said curve to generate an un-rebinned dataset; and
   perform a three dimensional backprojection on the un-rebinned dataset to generate an image.

26. A medium in accordance with claim 21, wherein to interpolate the obtained projection data, said program is configured to instruct a computer to interpolate the obtained projection data to generate interpolated data along a plurality of curves that cross at least two detector rows such that at least two curves are nonparallel.

27. A medium in accordance with claim 21, wherein to interpolate the obtained projection data, said program is configured to instruct the computer to interpolate the obtained projection data to generate a plurality of curves including two central curves, two exterior curves, and a plurality of intermediate curves between each central curve and a corresponding exterior curve, wherein the central curves and the intermediate curves cross at least two detector rows and the two exterior curves do not cross at least two detector rows, such that at least two central curves are parallel to each other and all the intermediate curves are non parallel each other, the two central curves, and the two exterior curves.

28. A medium in accordance with claim 27 wherein to interpolate the obtained projection data to generate at least one curve that crosses at least two detector rows, said program is configured to instruct the computer to generate a plurality of curves in accordance with:

$$z_i = k_i R \sin(\gamma) + b_i, i=0, 1, \ldots N-2, N-1,$$

where z represents a plane intersecting the detector, wherein the detector shape is cylindrical, $$k_0 = k_N = 0,$$

$$k_{\frac{N}{2}-1} = k_{\frac{N}{2}} = \tan \eta_0,$$

$$k_i = \frac{\frac{N}{2} - 2 - \left|i - \frac{N}{2} + 2\right|}{\frac{N}{2} - 2} \tan \eta_0 \quad i = 1, 2, \cdots \frac{N}{2} - 3, \frac{N}{2} - 2,$$

and $$k_i = \frac{\frac{N}{2} - 2 - \left|i - \frac{N}{2} - 1\right|}{\frac{N}{2} - 2} \tan \eta_0 \quad i = \frac{N}{2} + 1, \frac{N}{2} + 2, \cdots N-3, N-2,$$

wherein N is the number of detector rows of the cylindrical detector, and $\tan \eta_0 = (hNd)/(2\pi R)$ where h is a helical pitch, d is a detector row height, and R is a radius of the detector.

29. A medium in accordance with claim 27 wherein to interpolate the obtained projection data, said program is configured to instruct the computer to rebin data using an up-sampling factor of at least 2.

* * * * *